United States Patent
Klabunde et al.

(10) Patent No.: US 8,058,986 B2
(45) Date of Patent: Nov. 15, 2011

(54) METHOD FOR AUTOMATIC ASSOCIATION DEVICES TO A PATIENT AND CONCURRENT CREATION OF A PATIENT RECORD

(75) Inventors: Karin Klabunde, Bochum (DE); Heribert Baldus, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 949 days.

(21) Appl. No.: 11/719,162

(22) PCT Filed: Nov. 4, 2005

(86) PCT No.: PCT/IB2005/053617
§ 371 (c)(1),
(2), (4) Date: May 11, 2007

(87) PCT Pub. No.: WO2006/051464
PCT Pub. Date: May 18, 2006

(65) Prior Publication Data
US 2009/0231124 A1    Sep. 17, 2009

Related U.S. Application Data

(60) Provisional application No. 60/627,597, filed on Nov. 12, 2004.

(51) Int. Cl.
*G08B 1/08* (2006.01)
*H04Q 5/22* (2006.01)
(52) U.S. Cl. .................... 340/539.12; 340/10.1
(58) Field of Classification Search ............. 340/539.12, 340/10.1
See application file for complete search history.

(56) References Cited

U.S. PATENT DOCUMENTS

| | | | |
|---|---|---|---|
| 5,579,001 A * | 11/1996 | Dempsey et al. | 340/870.01 |
| 5,732,401 A * | 3/1998 | Conway | 705/29 |
| 6,454,708 B1 * | 9/2002 | Ferguson et al. | 600/300 |
| 6,579,231 B1 | 6/2003 | Phipps | |
| 6,642,845 B2 * | 11/2003 | Ishiwatari | 340/539.21 |
| 2004/0100376 A1 * | 5/2004 | Lye et al. | 340/539.12 |
| 2004/0104271 A1 * | 6/2004 | Martucci et al. | 235/472.01 |
| 2004/0153344 A1 * | 8/2004 | Bui et al. | 705/3 |
| 2005/0052290 A1 * | 3/2005 | Naden et al. | 340/993 |
| 2005/0212687 A1 * | 9/2005 | Nishikata | 340/825.72 |

(Continued)

FOREIGN PATENT DOCUMENTS

GB     2393072 A1     3/2004

(Continued)

OTHER PUBLICATIONS

Paul Lukowicz et al., "AMON: A Wearable Medical Computer for High Risk patient", Jul. 28, 2004 http://warable.ethz.ch/fileadmin/pdf_files/pub/iswc02_amon.pdf.

(Continued)

*Primary Examiner* — Benjamin C Lee
*Assistant Examiner* — Cal Eustaquio (57) ABSTRACT

A wireless patient point-of-care network (20) includes a plurality of medical devices (22, 24, 26) each with a wireless communication interface (46). Each medical device is configured to provide at least one medical service to a patient. A patient identification device (28) is associated with the patient. The patient identification device includes a wireless communication interface (46', 70) in communication with the wireless communication interfaces (46) of the medical devices. The patient identification device (28) performs a patient identification service that wirelessly associates the medical devices (22, 24, 26) with the patient.

23 Claims, 3 Drawing Sheets

U.S. PATENT DOCUMENTS

2005/0242946 A1* 11/2005 Hubbard et al. ......... 340/539.12
2011/0071702 A1* 3/2011 Wang et al. ..................... 701/2

FOREIGN PATENT DOCUMENTS

| WO | WO0128416 A1 | 4/2001 |
| WO | WO02064032 A2 | 8/2002 |
| WO | WO02067122 A1 | 8/2002 |
| WO | WO02069235 A2 | 9/2002 |
| WO | WO02101502 A2 | 12/2002 |
| WO | WO03043494 A1 | 5/2003 |
| WO | WO03085574 A1 | 10/2003 |
| WO | WO2004045410 A1 | 6/2004 |

OTHER PUBLICATIONS

Ephraim Schwartz, "InfoWord: Siemens to Pilot RFID Bracelets for Health Care", http://www.infoworld.com/article/04/07/23/HNrfidimplants__1.htmlJul. 29, 2004.

* cited by examiner

METHOD FOR AUTOMATIC ASSOCIATION DEVICES TO A PATIENT AND CONCURRENT CREATION OF A PATIENT RECORD

The following relates to the medical monitoring arts. It finds particular application in wireless patient point-of-care networks which are set up at a patient's bedside, and will be described with particular reference thereto. It finds more general application in providing wireless monitoring and therapy for a medical patient in substantially any setting, such as at the hospital, at home, or so forth.

A patient admitted to a hospital is typically connected with various types of electronic monitoring and therapy equipment, such an electrocardiograph (ECG), a blood pressure monitor, a blood oxygen saturation ($SaO_2$) sensor, an infusion pump for delivery of fluids, and so forth. These medical devices are used to diagnose and treat the patient.

Traditionally, medical devices used in bedside monitoring and therapy have been wired devices including an electrical power cord for powering the device and a communication cable for connecting the device to a nurses' station monitor, hospital network, or other electronic network. Sensors are traditionally connected with monitoring equipment by cabling as well. In such wired arrangements, it is relatively easy to identify which devices belong with a given patient.

The medical community is migrating toward wireless patient point-of-care networks. The continuing miniaturization of electronics, improved battery technology, and the advent of standardized low-power wireless communication protocols such as Bluetooth and ZigBee have enabled partly or completely stand-alone medical devices that have on-board electrical power and engage in wireless communication with other devices, display monitors, wireless hospital networks, or so forth. The reduction of wires in patient point-of-care networks has certain advantages, such as elimination of "wire routing" problems in setting up the patient point-of-care network, easier access by medical personnel to the patient, and improved patient mobility.

However, wireless patient point-of-care networks introduce new difficulties. In the wireless arrangement, identification of which equipment belongs with which patient is no longer straightforward. Indeed, even establishing the network to begin with is complicated by difficulty in ensuring that the invisible wireless connections are properly set up. Such difficulties are enhanced in critical care situations such as emergency rooms, where the wireless patient point-of-care network is constructed rapidly in a high-stress environment. Moreover, the patient point-of-care network should be modifiable by later addition or removal of devices, and should be portable to allow the patient to be temporarily or permanently moved during the hospital stay.

Existing wireless devices are typically associated with or assigned to the patient using a manual procedure, such as using a bar code or RFID reader, by marking the patient and corresponding devices with a marker, or by maintaining a centralized list of which devices are assigned with which patient (for example, on a blackboard mounted on a wall of the emergency room). Manual techniques are prone to human error, and result in delays in setting up or modifying the wireless patient point-of-care network.

In wireless patient point-of-care networks it is also more difficult to get an overview of which medical devices and services are available and are currently used for a specific patient. It is important to be able to determine which devices and services were used for a specific patient at what time.

The following contemplates improved apparatuses and methods that overcome the aforementioned limitations and others.

According to one aspect, a wireless patient point-of-care network is disclosed. A plurality of medical devices each including a wireless communication interface are each configured to provide at least one medical service to a patient. A patient identification device is associated with the patient. The patient identification device includes a wireless communication interface in communication with the wireless communication interfaces of the medical devices. The patient identification device performs a patient identification service that wirelessly associates the medical devices with the patient.

According to another aspect, a patient point-of-care method is provided. Medical services are provided to an associated patient using a plurality of medical devices. Each medical device includes a wireless communication interface and provides at least one medical service. A patient point-of-care method is performed using a patient identification device to manage all medical services that are provided by the devices being associated to one patient. This method allows determination of which medical devices and services are available in the patient point-of-care network and are currently used for the patient.

One advantage resides in providing a robust and secure link between data produced by medical devices and the patient.

Another advantage resides in automating the setup of the patient point-of-care network, optionally including automated setup of a patient record, to reduce the likelihood of manual errors compromising patient safety or privacy.

Yet another advantage resides in providing a readily expandable or modifiable wireless patient point-of-care network for providing medical services to a medical patient.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Figure 1:
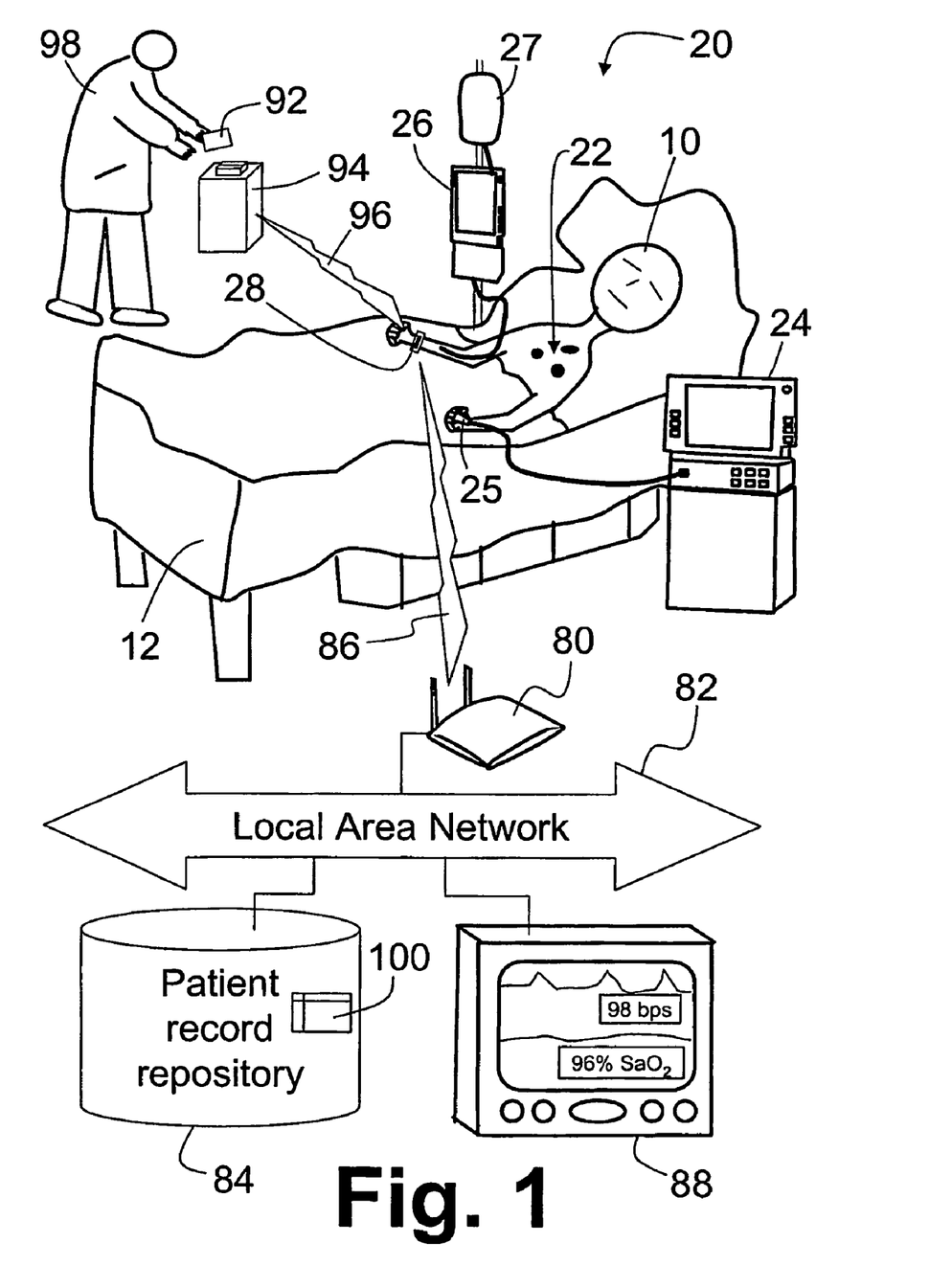
FIG. 1 illustrates an example wireless patient point-of-care network including a patient identification device worn by the patient.

With reference to FIG. 1, a medical patient 10 lies on a bed 12. A wireless patient point-of-care network 20 provides medical services such as vital signs monitoring and intravenous fluid therapy to the patient 10. In the illustrated example, the wireless patient point-of-care network 20 includes: (i) an autonomous wireless sensor network 22 which in the illustrated embodiment includes three sensor nodes disposed on the chest of the patient 10 to monitor vital signs such as electrocardiographic (ECG) data, heart rate, respiratory rate, respiratory cycle, blood pressure, or so forth; (ii) a blood oxygen saturation ($SaO_2$) monitor 24 connected with an $SaO_2$ fingertip probe 25; and (iii) an infusion pump 26 controlling intravenous delivery of fluid from a fluid bag 27. The wireless point-of-care network 20 is an example, and those skilled in the art can readily include additional or other medical devices in the network. Moreover, the wireless point-of-care network 20 can be changed on an ad hoc basis by adding or removing medical devices.

It will be appreciated that wires or cabling are not necessarily completely omitted from the wireless patient point-of-care network 20 for example, the SaO₂ fingertip probe is connected with the SaO₂ monitor 24 by a cable, and fluid transfer tubing connects the fluid bag 27 to the infusion pump 26 and connects the infusion pump 26 to the intravenous fluid delivery point in the right arm of the patient 10. Similarly, although not illustrated it is contemplated that some of the devices of the patient point-of-care network may include power cords connected to house electricity. For example, although the illustrated the SaO₂ monitor 24 is battery-powered, it could instead or additionally include a power cord plugged into a conventional electrical power outlet.

The patient point-of-care network 20 further includes a patient identification device 28. In the illustrated embodiment, the patient identification device 28 is disposed on a wristband worn by the medical patient 10; however, more generally the patient identification device can be worn or attached to the patient substantially anywhere. The medical devices 22, 24, 26 wirelessly communicate with the patient identification device 28, and optionally also wirelessly communicate with each other and/or with a hospital network. The patient identification device 28 optionally also includes patient monitoring or therapy functionality, such as an ECG, SaO₂, or other sensor.

Figure 2:
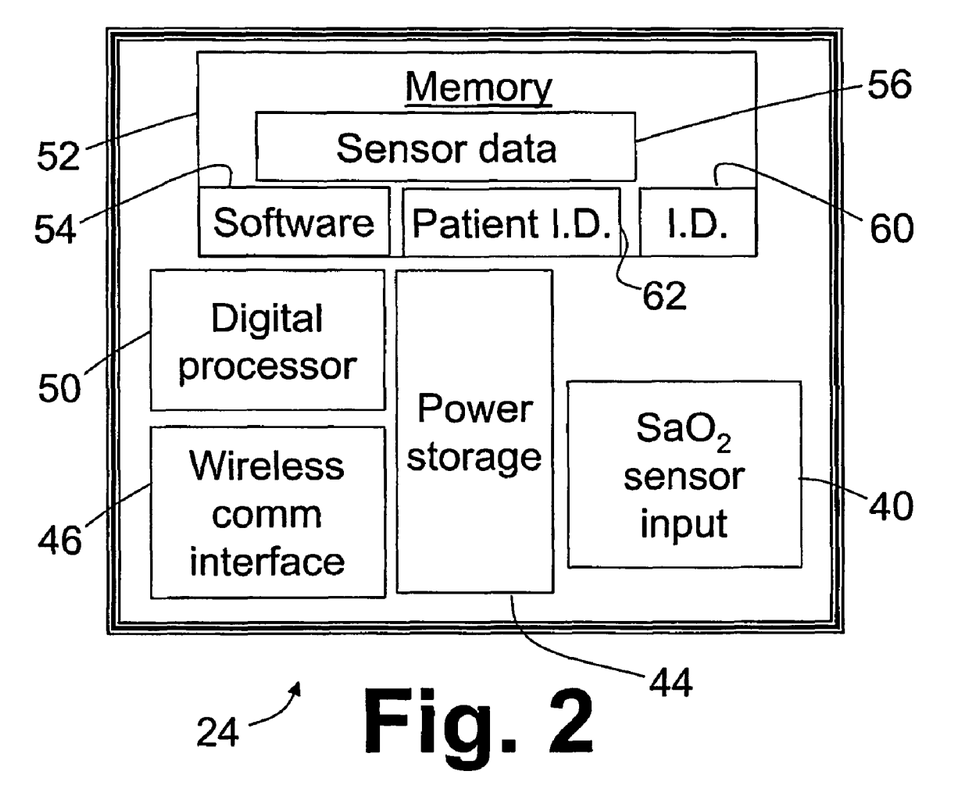
FIG. 2 diagrammatically illustrates the $SaO_2$ monitor of the patient point-of-care network of FIG. 1.

With continuing reference to FIG. 1 and with further reference to FIG. 2 which diagrammatically shows the illustrative SaO₂ monitor 24, typical components of the medical devices of the wireless patient point-of-care network are described. Each medical device is configured to provide one or more medical services, such as the SaO₂ monitoring service provided by the SaO₂ monitor 24 in conjunction with the fingertip sensor 25. The example SaO₂ monitor 24 has a sensor input 40 that receives data from the fingertip sensor 25. The monitor 24 further includes a power supply 44 and a wireless communication interface 46. The power supply 44 can be a rechargeable battery, storage capacitor, or other rechargeable power source, or can be a disposable battery. In some rechargeable power supply embodiments, the power supply 44 is wirelessly recharged, for example by exposure to infrared or radio frequency radiation. In other rechargeable power supply embodiments, the power supply 44 is recharged by connecting it with a battery charger. The wireless communication interface 46 typically employs a low power, short range communication protocol such as Bluetooth or ZigBee to conserve electrical power. In some embodiments, however, the wireless communication interface may include wireless local area network (WLAN) capability. Some medical devices may include more than one communication interface, such as a Bluetooth interface and a WLAN interface.

The monitor 24 further includes a digital processor 50 and a memory 52. A portion of the memory 52 is allocated to storing software 54 that is executable by the digital processor 50. In some embodiments, the portion of memory storing the software 54 is read-only. In other embodiments the software is stored in read/write memory and can be updated by uploading new program code into the memory 52, for example by wirelessly receiving software updates via the wireless communication interface 46. The software 54, when executed by the processor 50, performs the SaO₂ monitoring service. Another portion 56 of the memory 52 is allocated for storing sensor data acquired via the sensor input 40. The memory 52 also stores a device identifier 60, and a patient identifier 62 used to associate the monitor 24 with the patient 10. The stored device identifier 60 of each medical device 22, 24, 26 should be unique at least within a hospital department or floor; more preferably, the unique identifier 60 should be unique throughout the hospital or other medical facility to avoid the possibility of inadvertent wireless cross-talk with another nearby patient point-of-care network that includes another medical device with the same identifier.

Only the SaO₂ monitor 24 is illustrated in detail herein; however, it will be appreciated that the other medical devices 24, 26 of the wireless patient point-of-care network 20 are similarly configured to perform one or more medical services. While the SaO₂ monitor 24 provides only a single medical service (SaO₂ monitoring), some medical devices may provide more than one medical service. For example, the autonomous sensor node network 22 may provide several different medical services each monitoring a different vital sign. The illustrated wireless medical devices 22, 24, 26 each include on-board electrical power; however, some medical devices of the wireless patient point-of-care network may be powered via a power cord connected with an electrical outlet. Each of the wireless medical devices 22, 24, 26 stores the patient identifier 62 in memory to associate the devices 22, 24, 26 with the patient 10.

Figure 3:
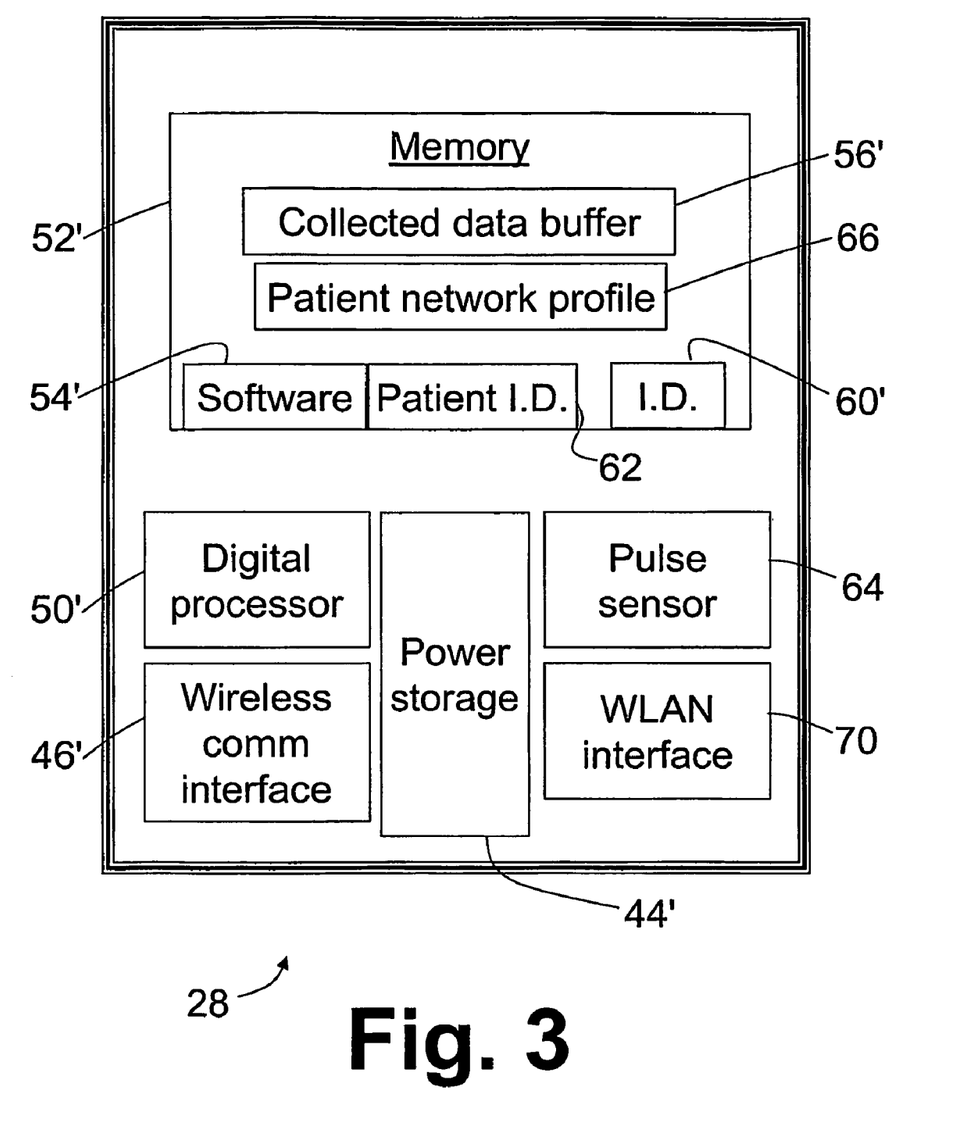
FIG. 3 diagrammatically illustrates the patient identification device of the patient point-of-care network of FIG. 1.

FIG. 3 diagrammatically shows components of the patient identification device 28. Similarly to the wireless medical devices 22, 24, 26, the patient identification device 28 includes a power supply 44', a wireless communication interface 46' employing a Bluetooth, ZigBee, or another low power, short range communication protocol, a digital processor 50' and a memory 52'. The memory 52' includes a portion allocated to storing software 54', and a portion 56' allocated for buffering data collected from the medical devices 22, 24, 26 of the patient point-of-care network 20. The memory further includes a portion allocated to store a unique device identifier 60', and a portion allocated to store the patient identifier 62.

In the illustrated embodiment, the patient identification device 28 collects sensor data from the monitoring devices 22, 24 and stores the collected sensor data in the buffer 56'. Optionally, data from the infusion pump 26, such as flow rate, is also collected in the buffer 56'. These data are collected via the wireless communication interfaces 46, 46'. In some embodiments, the patient identification device 28 is also configured to perform one or more medical services, such as a pulse monitoring service performed by an illustrative pulse sensor 64 of the patient identification device 28, or ECG, SaO₂, or other services. Pulse data collected by the sensor 64 or data generated by other medical services optionally provided by the patient identification device 28 are also collected and stored in the buffer memory portion 56'. In other embodiments, the patient identification device 28 performs no medical services of its own.

The patient identification device 28 coordinates the wireless patient point-of-care network 20. A patient network profile 66 is stored in an allocated portion of the memory 52'. The patient network profile 66 includes information about each medical device 22, 24, 26 in the wireless patient point-of-care network 20. Such information may include, for example, the device identifier 60 of each medical device and information about the services provided by that medical device. The patient identification device 28 further includes a wireless local area network (WLAN) interface 70 employing a WLAN protocol that is different from the low power, short range communication protocol employed by the wireless communication interfaces 46, 46'; accordingly, the WLAN interface 70 is not used to communicate with the wireless medical devices 22, 24, 26. Rather, the wireless communication interface 46' is used to communicate with the medical devices 22, 24, 26. In some embodiments, the WLAN protocol is an IEEE 802.11 WLAN protocol.

With returning reference to FIG. 1, the WLAN interface 70 of the patient identification device 28 communicates with a wireless access point 80 of a local area network 82 of the hospital or other medical facility to send data buffered in the memory portion 56' to a patient record repository 84 that stores patient records. In some embodiments, data is continuously transmitted to the patient record repository 84 rather than being buffered. This wireless data communication is diagrammatically indicated in FIG. 1 by a jagged connector 86. The collected data is stored at the patient record repository 84, displayed on a vital signs monitoring station or surveillance center 88, compared with previous sensor readings, or otherwise utilized for patient monitoring and treatment evaluation. Indeed, once collected data is sent to and stored in the patient record repository 84, it can be used by any device on the network 82 which has the proper authorization to access it. This situation is advantageous insofar as it enables efficient distributed access to vital patient point-of-care data; however, as this data constitutes private medical records, it is important to ensure that the data be properly identified with the patient and secured against unauthorized access.

In the illustrated embodiment the patient identification device 28 is used as a relay station for communicating data from the wireless medical devices 22, 24, 26 to the patient record repository 84. However, in some other embodiments the wireless medical devices 22, 24, 26 communicate directly with the patient record repository 84, either through the illustrated wireless communication interface 46 or through WLAN interfaces (not illustrated) included in the wireless medical devices. A combination can also be used, in which some medical devices relay data to the patient record repository 84 via patient identification device 28 while other medical devices include a WLAN interface and thus communicate directly with the patient record repository 84.

The patient identifier 62 is stored on the patient identification device 28 and on each of the medical devices 22, 24, 26 to associate the devices with the patient 10. Optionally, the patient network profile 66 stored on the patient identification device 28 includes additional patient information. Such additional patient information may include, for example, a patient name, a patient number or other unique patient identifier, and optionally other information about the patient such as information about the patient's drug allergies, a list of the patient's prescribed drugs, and so forth. By storing such critical information on the patient identification device 28, it can be accessed when the patient is moved to a new room or other new location and checked before the patient is medicated or otherwise treated at the new location. For example, medical personnel may use a personal data assistant (PDA), laptop computer, or other user interface to wirelessly access the patient identification device 28 via either the wireless communication interface 46' or the WLAN interface 70 and read the patient information contained in the patient network profile 66. Such an access may be performed after the patient has been moved to a new room, if the patient is unconscious or uncommunicative and a question arises about the patient's identity, or so forth. Such an access may also be performed just prior to the first administration of a new medication, to determine whether the new medication is contraindicated by patient allergies, medical history, possible adverse reaction with another medication currently prescribed to the patient, or so forth.

Such additional patient information stored in the patient network profile 66 can be gathered and communicated to the patient identification device 28 in various ways. In one approach which is illustrated in FIG. 1, a medical card 92 belonging to the patient includes the relevant patient information electrically encoded on a magnetic strip, optical strip, or other electronically readable data store. The encoded information is read by a card reader 94 and wirelessly transmitted from the card reader 94 to the patient identification device 28 via the wireless communication interface 46' or via the WLAN interface 70. This communication of patient information is diagrammatically indicated in FIG. 1 by a jagged connector 96. In one suitable procedure, a hospital admissions person 98 swipes the patient card 92 during the admissions process and wirelessly transfers the information to the patient identification device 28. The patient identification device 28 is then attached to the patient 10 as a wristband. Alternatively, the patient identification device 28 can be attached first, and then loaded with the patient information.

If a medical card is available, the unique patient identifier is suitably derived from the medical card. However, in some cases, the patient may not have a medical card that is readable by the card reader 94. In such cases, a temporary guest card can be loaded with the requisite patient information and processed in the same way as the medical card 92 to generate a unique patient identifier, or a unique patient identifier and optionally other information can be collected and transferred to the patient identification device 28 in another manner. In some embodiments, the guest card already contains a suitable unique patient identifier which can be assigned to the newly admitted patient.

The software 54 of the medical devices 22, 24, 26 is generally limited to implementing the medical services provided by those medical devices, and to wirelessly connecting with and sending data to the patient identification device 28. Optionally, the software 54 is capable of performing further operations, such as detecting a low battery and sending a wireless low battery warning message out.

The software 541 of the patient identification device 28 is generally more sophisticated, including the ability to initialize and update the patient network profile 66, receive and store data from the medical devices 22, 24, 26 in the buffer 56', connect with the local area network 82 via the WLAN interface 70, transfer buffered data to the patient record repository 84, and transfer information contained in the patient network profile 66 over the WLAN interface 70 upon receiving a properly authorized request for this patient information. In some embodiments, this functionality is organized as services performed by the patient identification device 28. Thus, the patient identification device 28 provides services such as a patient identification service for associating a medical device with the patient 10, a buffer transfer service for transmitting buffered data to the patient record repository 84, and so forth. The patient network profile 66 typically includes information about all medical devices of the patient point-of-care network 20 and information about the services provided by each medical device.

The wireless patient point-of-care network 20 is established as follows. The patient identification device 28 is initialized with at least the patient identifier 62 as previously described and is placed on or attached to the patient 10. A new patient record 100 corresponding to the patient 10 is created on the patient record repository 84. In some embodiments, the new patient record 100 is created manually. In some other embodiments, the patient identification device 28 automatically creates a new patient record 100 at the patient record repository 84 as part of the patient point-of-care network initialization. For example, after patient information is loaded onto the patient identification device 28, in these embodiments the patient identification device 28 connects with the local area network 82 via the WLAN interface 70, accesses the patient record repository 84, instructs the patient record repository 84 to create the new patient record 100, and initializes the new patient record 100 by transferring the patient information including the patient identifier 62, information about the patient identification device 28, and other information stored in the patient network profile 66 to the new patient record 100. Thereafter, when data tagged with the patient identifier 62 is sent to the patient record repository 84, it is directed toward and stored in the new patient record 100, thus enabling the collected data to be identified with the patient 10.

After installing the initialized patient identification device 28 on the patient 10, the various wireless medical devices 22, 24, 28 can be added in an ad hoc manner to construct the wireless patient point-of-care network 20. As each new medical device is added to the patient point-of-care network 20, it is identified with the patient 10 and registered with the patient identification device 28 using a patient identification service executed by the patient identification device 28. The registration processing includes at least sending the patient identifier 62 to the new medical device and updating the patient network profile 66 at the patient identification device 28 with information about the new medical device including for example the device identifier and information about medical services provided by the new medical device. These registration operations can be performed in various ways.

In some embodiments, the patient identification device 28 periodically wirelessly polls for new medical devices using the wireless communication interface 46' and, when a new medical device is detected, executes the patient identification service to transmit the patient identifier 62 to the new medical device and to update the patient network profile 66. The next time the patient identification device 28 connects with the patient record repository 84, it also updates the patient record 100 regarding the new medical device.

To ensure that the new medical device associates with the correct patient point-of-care network, the patient identification service can be initiated by the new medical device in response to an action by a medical person. For example, a "connect" button can be provided on the medical device, which the medical person presses when the devices is installed at the point-of-care. When the connect button is pressed, the new medical device wirelessly connects with the patient identification device 28 and requests that the patient identification device 28 execute the patient identification service to initialize the new medical device with the patient identifier 62 and to transfer information about the new medical device to the patient network profile 66. Alternatively, the medical person may use a personal data assistant (PDA) to connect with the patient identification device 28 and request that it execute the patient identification service to initialize the new medical device.

In another variation, the patient identifier 62 can be first loaded into the new medical device by a physician or other medical person using a personal data assistant (PDA), laptop computer, or other electronic user interface capable of wirelessly communicating with the new medical device. Then, when the patient identification device 28 detects the new medical device by polling, it first checks to see whether the new medical device has a patient identifier that matches the patient identifier 62 stored in the patient identification device 28. If the patient identifiers match, then the patient identification device 28 executes the patient identification service to add the new medical device to the patient network profile 66.

In yet another variation, the new medical device directly makes a connection request to the patient identification device 28, which then checks whether the patient identifier is correct.

In still yet other embodiments, the patient identification device 28 does not automatically add the new medical device to the patient network profile 66. Rather, in these embodiments the patient network profile 66 is manually updated by a physician or other medical person using a PDA or the like that wirelessly connects with the patient identification device 28.

In a similar manner, when a medical device is removed from the patient point-of-care network 20 or is disabled by a malfunction of the medical device, the patient identification device 28 suitably updates the patient network profile 66 by executing a device removal service. In some embodiments, the patient identification device 28 periodically polls the medical devices of the patient point-of-care network 20 and, when communication with one of the medical devices ceases, removes information about that medical device from the patient network profile 66. Alternatively, the medical device may include a "disconnect" button which, when pressed, causes the medical device to send a request to the patient identification device 28 asking that the medical device be removed from the patient network profile 66. In still yet another approach, the medical device can be removed from the patient network profile 66 manually by a physician or other medical person using a PDA or other electronic user interface capable of wirelessly communicating with the patient identification device 28.

In some embodiments, the wireless patient point-of-care network 20 operates autonomously most of the time. Occasionally, the patient identification device 28 polls to locate the available wireless access point 80 of the local area network 82 and, if it identifies the available wireless access point 80, makes a network connection and transfers collected data to the patient record 100 of the patient record repository 84. On the other hand, if the polling finds that no wireless access point is available (for example, if the patient is ambulatory and out of range of any wireless access points) then the wireless patient point-of-care network 20 continues to operate autonomously to collect and store data and to delivery therapy such as intravenous fluids. Once a network connection is reestablished, the collected data is uploaded to the patient record 100 of the patient record repository 84. In other embodiments, vital sign data is continuously transmitted to the patient record repository 84 via the network connection without buffering or otherwise storing the data at the patient identification device 28. In these embodiments, data collected during an interruption in the network connection is lost, or alternatively data buffering at the patient identification device 28 is employed only in the event of a network connection interruption to prevent such data loss.

Another advantage of providing the patient network profile 66 on the patient identification device 28 attached to the patient 10 is that it enables rapid assessment of the available medical services provided by the patient point-of-care network 20. For example, considering the autonomous sensor node network 22, not all of the vital signs sensors of this medical device may be initially active. However, all the available medical services, and their status as active or inactive, are listed in the patient network profile 66. Hence, a physician or other medical person can review the patient network profile 66 using a PDA or other device to determine whether a vital sign sensor of interest is already available and if so whether its status is active or inactive. This provides an overview of which medical devices and services are currently available and used for a patient in his or her associated patient point-of-care network.

Moreover, in some embodiments all data stored in the patient network profile 66, including the continuously updated listing of available medical services and the status of each medical service as active or inactive, is logged in the patient record 100 of the patient record repository 84. This log of data including the continuously updated listing of active and inactive medical services provides detailed documentation of the medical care provided to the patient throughout the patient's stay at the hospital or other medical facility, including logs of which medical devices and corresponding services were used for the patient 10 at which time. The patient record 100 at the patient record repository 84 stores all information related to one patient and his or her patient point-of-care network (i.e. patient identifier 62, patient data, medical devices 22, 24, 26, services provided, services used, and so forth.

The patient record 100 can be maintained at the patient record repository 84 after the patient 10 is discharged from the hospital, providing a permanent record of services given to the patient that may be useful in resolving billing discrepancies, maintaining the patient's medical history, providing evidence in legal proceedings, or for other purposes. On the other hand, the patient identification device 28 can be re-initialized and used for another newly admitted patient.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A wireless patient point-of-care network comprising:
   a plurality of medical devices each including a wireless communication interface and each configured to provide at least one medical service to a patient; and
   a patient identification device associated with and worn by or attached to the patient, the patient identification device including a wireless communication interface in communication with the wireless communication interfaces of the medical devices via a short range wireless communication protocol, the patient identification device performing a patient identification service via the short range wireless communication protocol that wirelessly associates the medical devices with the patient when the patient identification device is within communication range of the wireless communication interfaces of the medical devices.

2. The wireless patient point-of-care network as set forth in claim 1, wherein the patient identification device stores patient information including at least a patient identifier, and the performing of the patient identification service includes wirelessly communicating the patient identifier to the medical devices.

3. The wireless patient point-of-care network as set forth in claim 2, wherein the performing of the patient identification service further includes updating a patient network profile stored on the patient identification device with information about each of the medical devices of the wireless patient point-of-care network and information about medical services provided by each medical device.

4. The wireless patient point-of-care network as set forth in claim 1, wherein the wireless communication interface of the patient identification device includes:
   a first wireless communication interface configured to communicate with the wireless communication interfaces of the plurality of medical devices via the short range wireless communication protocol; and
   a wireless network interface different from the first wireless communication interface, the patient identification device receiving data from the medical devices using the first wireless communication interface and relaying the received data to a patient record repository via the wireless network interface.

5. The wireless patient point-of-care network as set forth in claim 4, wherein:
   the wireless communication interfaces employ one of a Bluetooth wireless communication protocol and a ZigBee wireless communication protocol; and
   the wireless network interface employs a wireless local area network (WLAN) protocol.

6. The wireless patient point-of-care network as set forth in claim 1, wherein the patient identification device stores a patient network profile containing information about each of the plurality of medical devices.

7. The wireless patient point-of-care network as set forth in claim 6, wherein the patient identification device includes:
   stored software; and
   a processor that selectively executes at least selected portions of the stored software to perform selected patient network services including at least: (i) updating the patient network profile to add a medical device to the wireless patient point-of-care network, and (ii) updating the patient network profile to remove one of the medical devices from the patient point-of-care network.

8. The wireless patient point-of-care network as set forth in claim 7, wherein the updating performed by the processor includes (i) wirelessly detecting a proximate new medical device and (ii) wirelessly detecting removal of or cessation of communication with one of the medical devices of the wireless patient point-of-care network.

9. The wireless patient point-of-care network as set forth in claim 6, wherein the patient identification device includes:
   stored software; and
   a processor that selectively executes at least selected portions of the stored software to perform selected patient network services including at least communicating with an associated user via the wireless communication interface to selectively add a medical device to or remove a medical device from the patient network profile.

10. The wireless patient point-of-care network as set forth in claim 6, wherein the patient identification device includes:
    stored software; and
    a processor that selectively executes at least selected portions of the stored software to (i) receive patient information via the wireless communication interface and (ii) communicate the received patient information to an associated patient record repository via the wireless communication interface to create a new patient record on the associated patient record repository.

11. The wireless patient point-of-care network as set forth in claim 1, wherein the patient identification device further includes:
    means for performing at least one medical service.

12. The wireless patient point-of-care network as set forth in claim 1, wherein the patient identification device is worn by the patient.

13. A system comprising:
    the wireless patient point-of-care network of claim 1; and
    a patient record repository containing a patient record associated with the patient, the patient record storing at least data received from the wireless patient point-of-care network via one or more of the wireless communication interfaces.

14. The patient point-of-care system as set forth in claim 13, further including:
   a means for communicating patient information to the patient identification device, said patient information subsequently being communicated from the patient identification device to the patient record repository via the wireless communication interface of the patient identification device to create the patient record.

15. The patient point-of-care system as set forth in claim 14, wherein the means for communicating patient information includes:
   a card reader that (i) reads the patient information from one of a patient medical card and a guest card and (ii) communicates the read patient information to the patient identification device.

16. The patient point-of-care system as set forth in claim 13, further including:
   a patient network profile stored at least at one of (i) the patient identification device and (ii) the patient record of the patient record repository, the patient network profile including information about each of the medical devices of the wireless patient point-of-care network, the patient network profile being updated as medical devices are added to or removed from the wireless patient point-of-care network.

17. A patient point-of-care method comprising:
   attaching a patient identification device to a patient;
   providing associated medical services to the patient using a plurality of medical devices, each medical device including a wireless communication interface and providing at least one medical service;
   performing a patient identification service using the patient identification device in wireless communication with the medical devices to wirelessly associate each of the medical devices with the patient; and
   maintaining an updateable patient network profile at the patient identification device including at least identifying information pertaining to each medical device and information about the one or more medical services each medical device is configured to provide
   wherein the performed patient identification service includes at least sending a patient identifier to the medical devices and updating the patient network profile at the patient identification device with information about the medical devices when the patient identification device is within communication range of the wireless communication interfaces of the medical devices.

18. The patient point-of-care method as set forth in claim 17, wherein the patient network profile further includes information pertaining to the patient, the method further including:
   wirelessly communicating the information pertaining to the patient from the patient identification device to an associated patient record repository to create a new patient record corresponding to the patient on the patient record repository; and
   wirelessly communicating data generated by the medical devices to the new patient record.

19. The patient point-of-care method as set forth in claim 18, further including:
   reading one of a patient medical card and a guest card containing the information pertaining to the patient, said read information being communicated to the patient identification device.

20. The patient point-of-care method as set forth in claim 17, further including:
   detecting a new medical device to be added to the patient network profile; and
   repeating the patient identification service using the patient identification device in wireless communication with the new medical device to wirelessly associate the new medical device with the patient.

21. The patient point-of-care method as set forth in claim 17, further including:
   detecting a loss of communication with a removed or disabled one of the plurality of medical devices; and
   updating the patient network profile at the patient identification device to remove identifying information pertaining to the removed or disabled medical device.

22. The patient point-of-care method as set forth in claim 18, further including:
   logging information from the patient network profile to an associated patient record repository to generate a continuous record of medical services provided to the associated patient.

23. The wireless patient point-of-care network as set forth in claim 1, wherein each medical device of the plurality of medical devices is configured to provide at least one medical service to the patient selected from the group of medical services consisting of monitoring of a patient vital sign and providing an intravenous fluid therapy to the patient.

* * * * *